Figure 1:
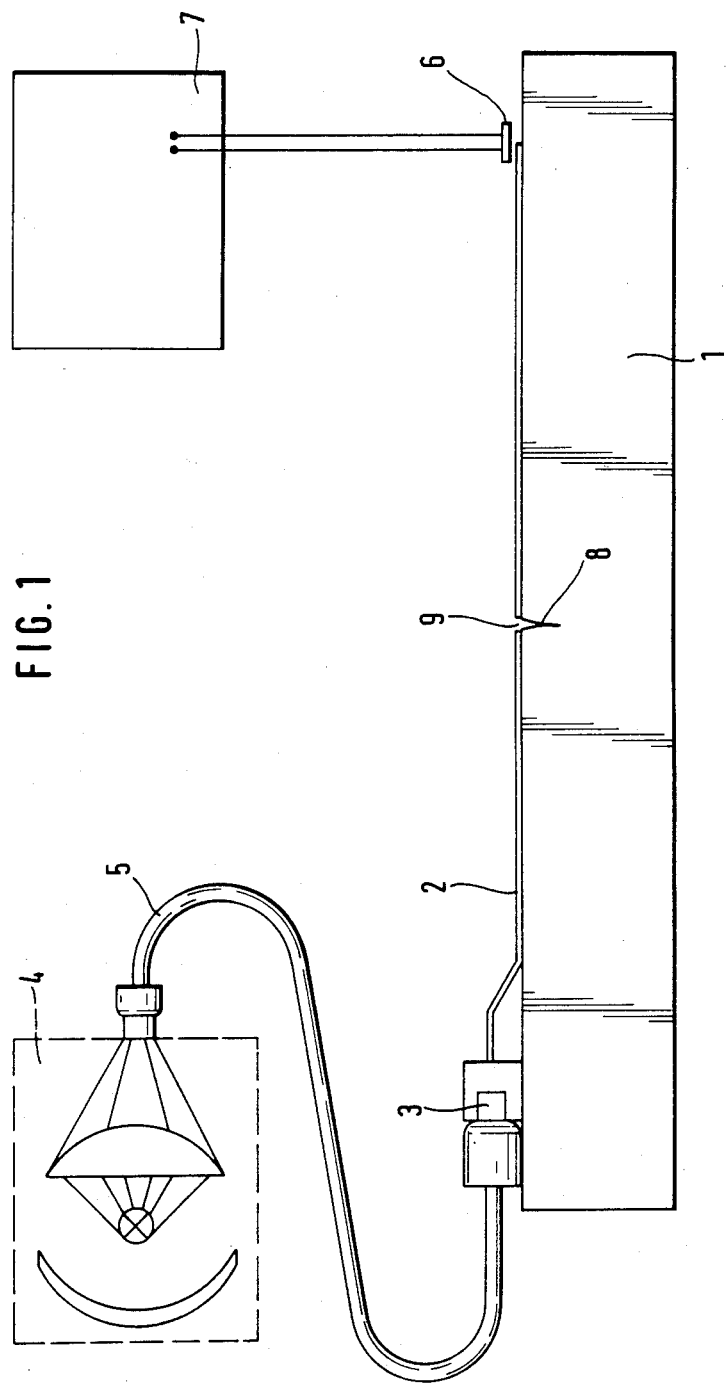

United States Patent [19]

Malek et al.

[11] Patent Number: 4,629,318
[45] Date of Patent: Dec. 16, 1986

[54] MEASURING DEVICE FOR DETERMINING CRACKS

[75] Inventors: Samir Malek, Schwanewede-Leuchtenburg; Bernd Hofer, Lemwerder, both of Fed. Rep. of Germany

[73] Assignee: VFW GmbH, Bremen, Fed. Rep. of Germany

[21] Appl. No.: 438,864
[22] PCT Filed: Feb. 25, 1982
[86] PCT No.: PCT/DE82/00069
   § 371 Date: Oct. 22, 1982
   § 102(e) Date: Oct. 22, 1982
[87] PCT Pub. No.: WO82/03454
   PCT Pub. Date: Oct. 14, 1982

[30] Foreign Application Priority Data

Mar. 26, 1981 [DE] Fed. Rep. of Germany ....... 3111858
Oct. 26, 1981 [DE] Fed. Rep. of Germany ....... 3142392
Feb. 25, 1982 [DE] Fed. Rep. of Germany ....... 3206656

[51] Int. Cl.[4] .......................................... G01B 11/16
[52] U.S. Cl. .................................... 356/237; 250/227
[58] Field of Search ...................... 356/32, 32.5, 237; 250/227; 73/800

[56] References Cited

U.S. PATENT DOCUMENTS 3,910,105 10/1975 Hoffstedt .......................... 356/32 X

FOREIGN PATENT DOCUMENTS 2937824 10/1980 Fed. Rep. of Germany ........ 73/800
1570511 7/1980 United Kingdom .

OTHER PUBLICATIONS

Korth, "Integrated Optical Force and Stress Sensor", *IBM Tech. Disclos. Bull*, vol. 24, No. 2, pp. 893–894, 7/81.

Primary Examiner—Davis L. Willis
Assistant Examiner—Matthew W. Koren
Attorney, Agent, or Firm—Ralf H. Siegemund

[57] ABSTRACT

The invention relates to a measuring device for determining cracks. Light conductive fibers or film are provided as crack detectors in this measuring device which fibers or films are applied directly upon the construction parts. Light is coupled into these light conductive fibers by means of a coupler and the passage of light is monitored at the free end. A fiber fracture serves as irreversible crack indication.

15 Claims, 18 Drawing Figures

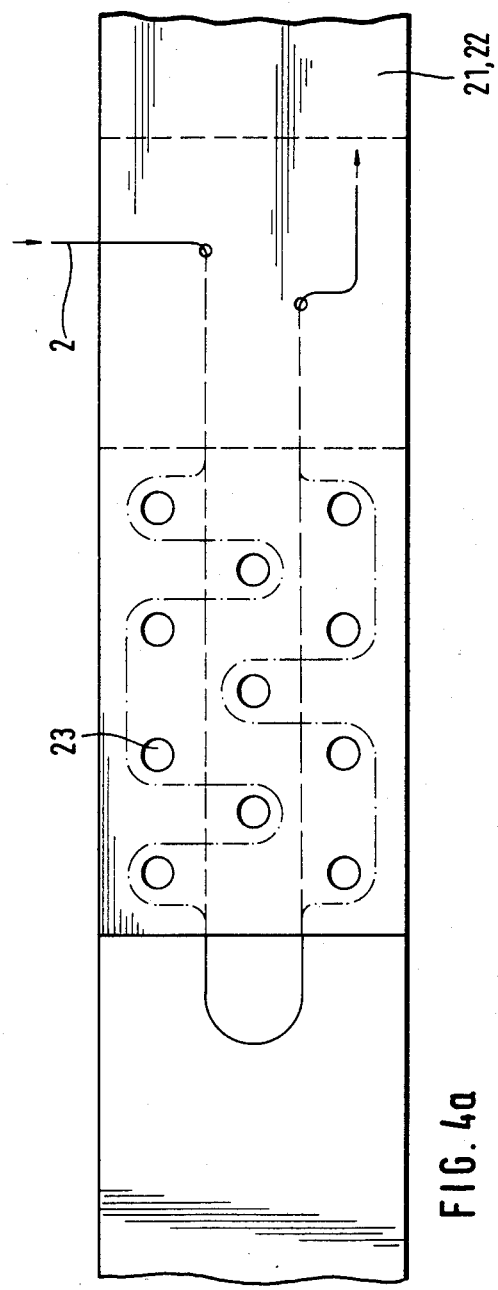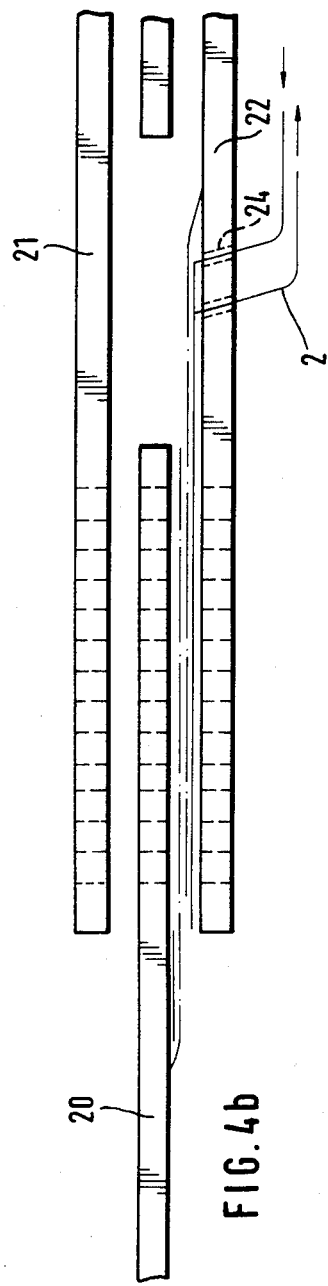
FIG. 4a
FIG. 4b

FIG. 5
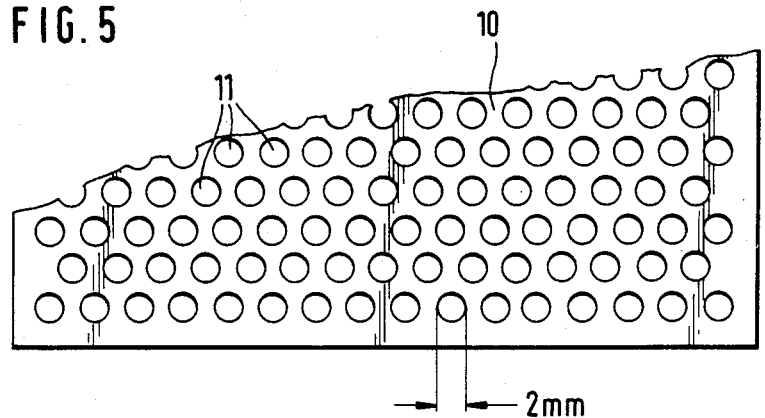
FIG. 6a
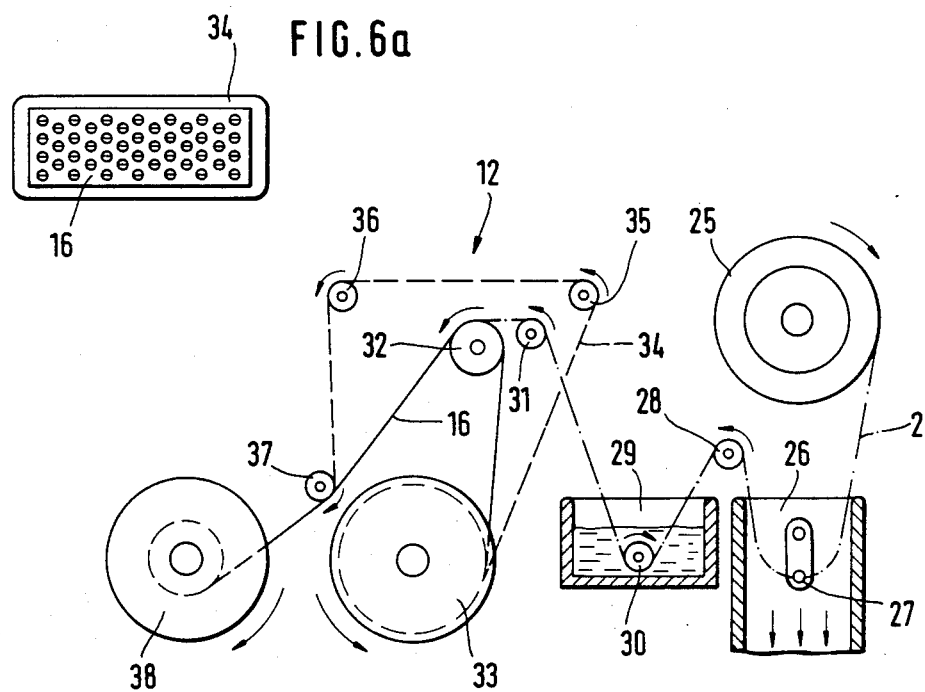
FIG. 6

FIG. 7
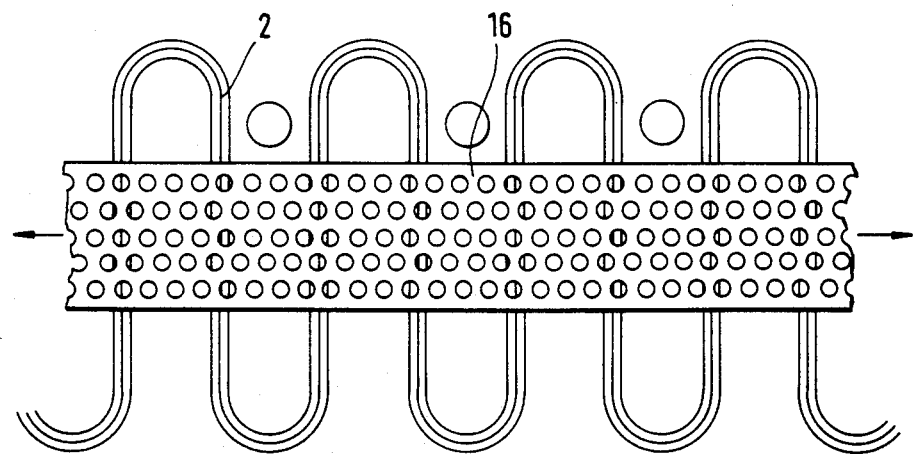
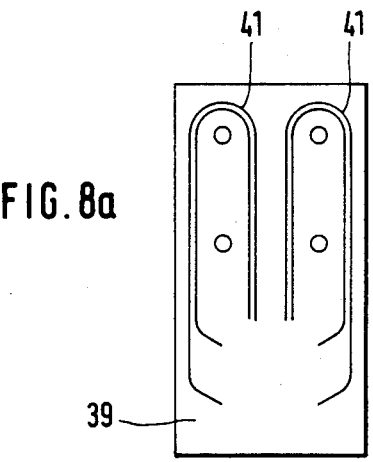
FIG. 8a
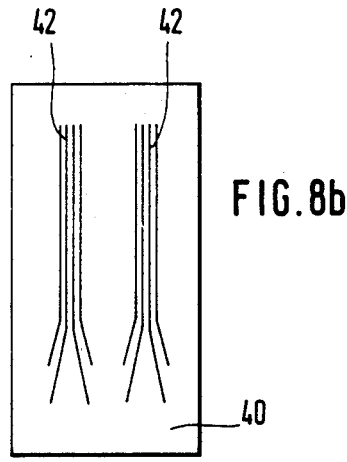
FIG. 8b

FIG. 9a
FIG. 9b
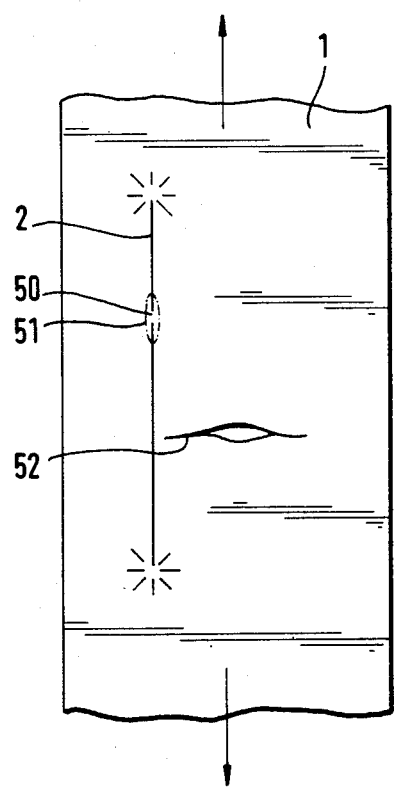
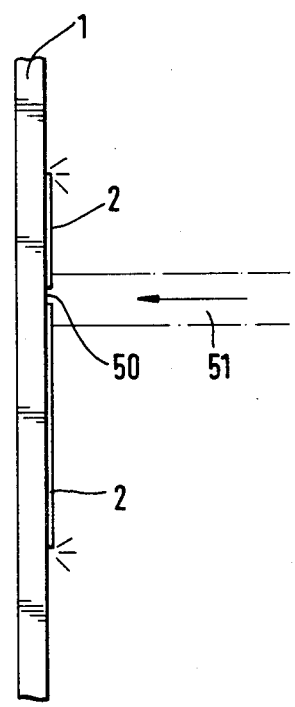

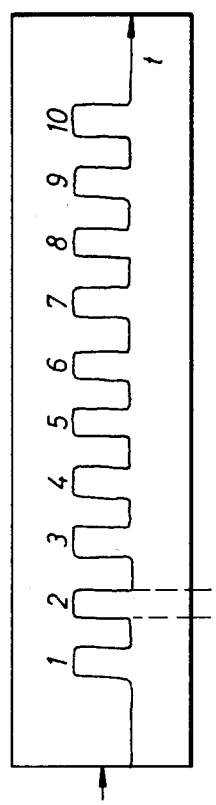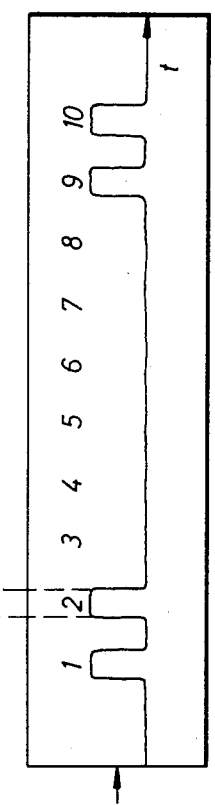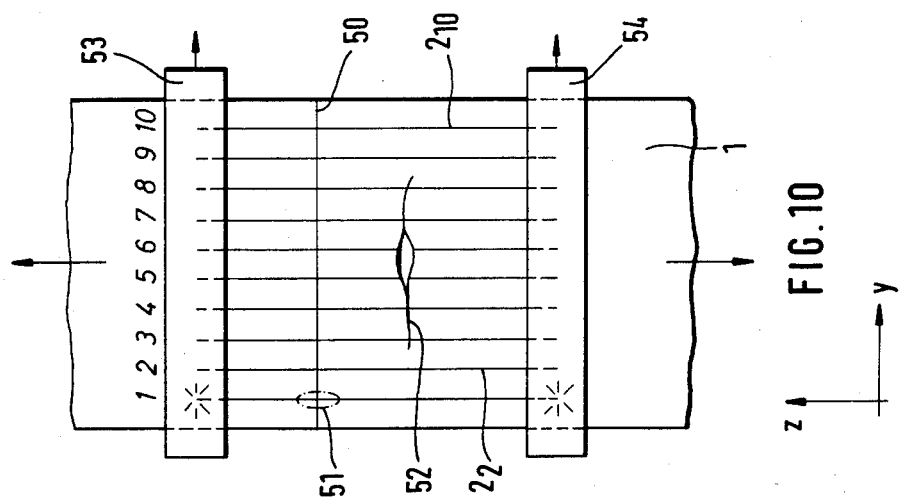

MEASURING DEVICE FOR DETERMINING CRACKS

The invention relates to a measuring device for determining cracks in test objects by means of a crack detector which is comprised of light conductive fibers to be applied upon test objects which crack detector produces a signal for indicating a crack in the case of occurence of cracks.

It is customary in aircraft and other structure components to use measuring devices for determining cracks. There is a pronounced demand for such measuring devices which are also called crack sensors because an early recognition (of such cracks) in operating aircraft and other structure components as well as during tests make possible a suppression of interference at a sufficiently early time.

It is known for determining cracks to paste a wire upon the component, the wire being provided with an insulated jacket coating, and to use the fracture of the wire resulting from a crack for purposes of indicating the crack. Pursuant to this method, an electrical current is run through the wire which collapses when the wire fractures and triggers the crack indication in an evaluating electronic circuit. In accordance with another method for determining cracks, the respective component is provided in its entirety with an insulating layer and subsequently conductor strips are sprayed on which, just as aforedescribed trigger a crack indication upon fracture. Both methods have some drawbacks. First of all, the required insulating layer between the component and the crack identifying conductors reduce the detection sensitivity. Moreover in the case of outdoor use and particularly upon employing silver conducting lacquer, one has to expect corrosion problems which renders impossible for practical reasons any long lasting monitoring. Moreover, silver conducting lacquer is very expensive and furthermore, the depositing of conductor strips is rather expensive and troublesome. Finally, only a temporary interruption may occur upon a fracture of the conductor strips or wires, for example, because the load has abated which leads to a reclosing of the electric circuit. Moreover, the strips or wires are subject to electromagnetic interferences in the environment. This way a crack indication may be extinguished again and a non-existing freedom from cracks may be simulated.

Therefore it is an object of the invention to provide a measuring device for determining cracks in accordance with the kind mentioned in the beginning which however, guarantees always a reliable and irreversible crack indication. This object is obtained in accordance with the invention through the characterizing features of the main claim.

Further developments and advantageous embodiments of the invention can be taken from the dependent claims.

Figure 2:
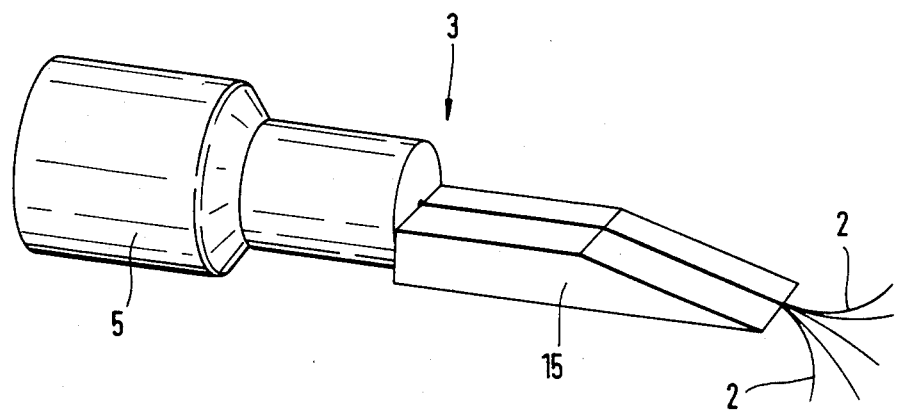
Figure 3:
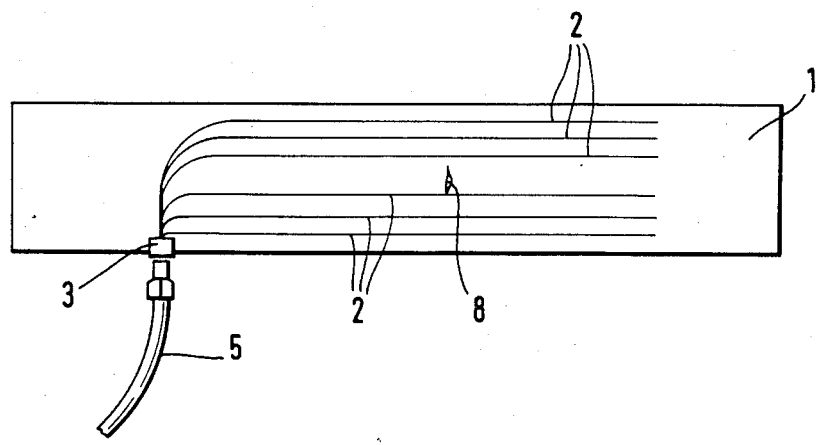

The invention is more fully explained with reference to the appended drawings. There is shown in:

FIG. 1, the principle of a measuring device for determining cracks,

FIG. 2, a light coupler,

FIG. 3, a construction part provided with light conducting fibers, and

Figure 12:
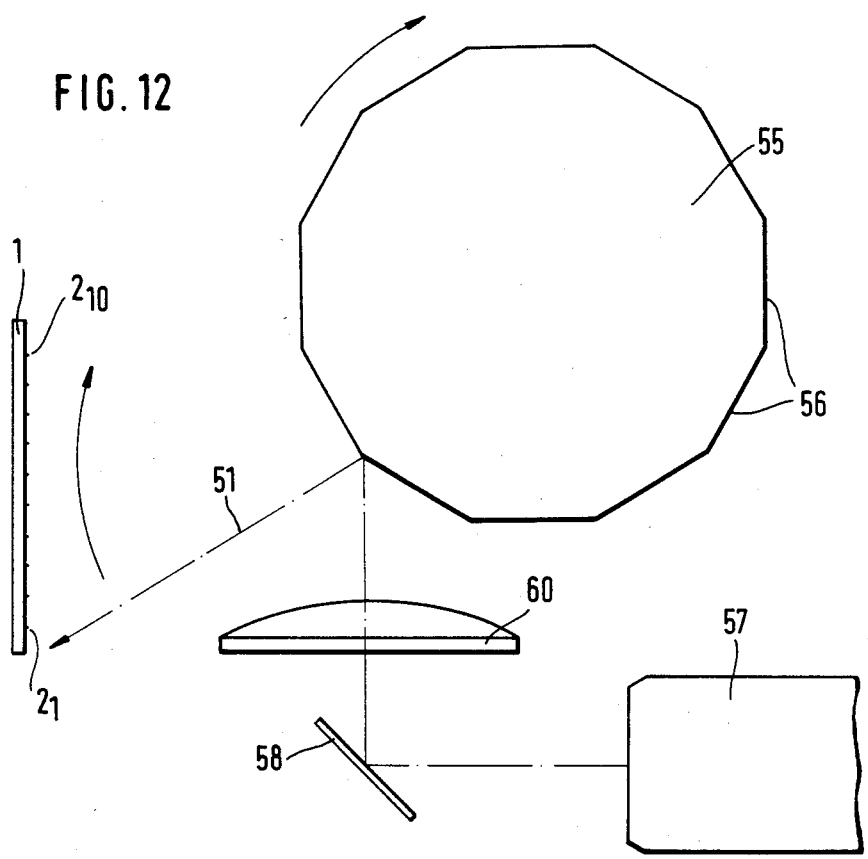
Figure 13:
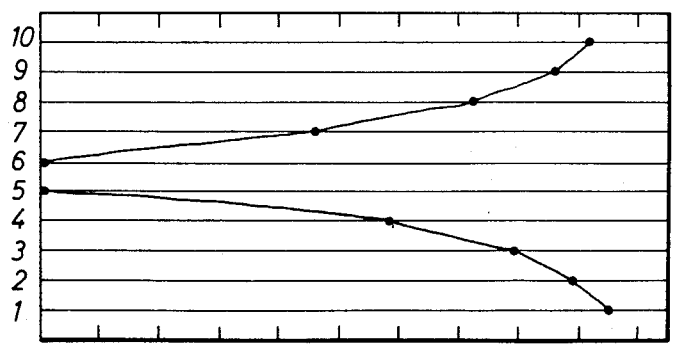

FIG. 4, a structure connection with attached light conducting fibers,

FIG. 5, a perforated adhesive foil ribbon,

FIG. 6, a device for placing light conducting fibers upon a adhesive foil ribbon, FIG. 6a, an adhesive foil ribbon provided with light conducting fiber, FIG. 7, an adhesive foil ribbon with light conducting fibers placed in a meander pattern, FIG. 8, two templates for placing light conducting fibers in a special configuration, FIGS. 9a and 9b, the principle for producing an indication of the progression of a crack, FIG. 10, a construction part provided with numerous light conducting fibers, FIGS. 11a and 11b, two signal diagrams, FIG. 12, a construction part which is periodically inspected by means of a light deflector, and FIG. 13, a diagram showing crack progression.

The principle of a measuring device for determining cracks is illustrated in FIG. 1 wherein a light conducting fiber 2 is pasted to a construction part 1 by means of a suitable adhesive. The light conducting fiber 2 which may be comprised of glass, quartz or synthetic material, is applied to the construction part 1 directly i.e. without insulating layer. Concerning the use of synthetic material, vapor deposited light conductive films can be used here to serve as light conducting fibers. The application or placement of the fibers is carried out by means of depositing lacquer, preferably a two component zinc chromate lacquer. The fibers are therefore embedded in a protecting lacquer layer and adhere therewith intimately upon the construction part. This adhering withstands the loads as they occur during use particularly high temperatures. The light conducting fiber 2 is provided with light at one end by means of a light coupler 3 which light is provided from a light source 4 via a feeder light conductor 5. A light detector 6 is provided at the other end of the light conducting fiber 2 which light detector converts the received light into an electrical quantity and conducts same through twin conductors to an evaluating electronics 7. A crack 8 indicated in the construction part 1 produces therefore a fracture 9 in the light conducting fiber 2 which fracture is irreversible and remains even upon a load relief upon the construction part 1.

The fracture 9 produced in the light conducting fiber reduces the light transmission very strongly so that the light detector signals likewise strongly change electrical quantities to the evaluating electronics 7. It is possible to ascertain the crack if not yet visible (by and in itself) through emergence of light at the point 9 of fracture and one ascertains additionally an indication of the location of the crack. Theoretical studies have yielded the result that the crack detection sensitivity is inversely proportional to the diameter of the fiber. These studies were verified through first, practical tests. For example, very good sensitivity in the case of aluminum structure parts or aluminum structure joints was obtained under utilization of glass fibers having a diameter from 30 micrometers to 60 micrometers and under further utilization of a conventional two component epoxy adhesive.

FIG. 2 illustrates the details of a light coupler 3 in which a ramp 15 forms the transition from the feeder light conductor 5 to the light conducting fibers 2. Half of this ramp 15 is configured for purposes of connection to the feeder light conductor 5 as a parallelpiped which is continued in a wedge so that there is a clearcut transition from the light conducting fiber 2 to the respective construction part. The width of the ramp is chosen so that several light conducting fibers can be connected to the feeder light conductor 5 without difficulty.

A construction part 1 can be seen in the illustration of FIG. 3 upon which part six light conducting fibers 2 are bonded in a parallel position in longitudinal direction. The six light cnducting fibers lead to a common light coupler 3 on one end which light coupler receives light via a feeder light conductor 5 from a light source which is not illustrated. A crack 8 is shown in construction part 1 which crack migrates from the center and underneath light conducting fibers 2. It is possible to have a control person visually observing the end of the light conducting fibers 2 or each of the light conducting fibers is provided with a light detector as shown in FIG. 1 for continuous observation and evaluation in an evaluating electronics 7 as shown in FIG. 1.

In the last illustration in accordance with FIG. 4 a structure part joint or connection is seen in which a light conducting fiber 2 is employed for continuous monitoring as to cracks. The structure joint is comprised of a plate element 20 whose depicted end is connected to two plate elements 21 and 22 disposed on the two sides of element 20. The joint is riveted as indicated in FIG. 4a by the bores 23. As can also be seen from FIG. 4a, the light conducting fiber 2 is guided by means of a longitudinal loop around the central row of bores 23. However, as indicated in dash-dot lines, it is also possible to install the light conducting fiber in a meander pattern. The light conducting fiber 2 is run on the outside through oblique boreds 24 which are provided in the plate element in order to couple light thereto without impediments so that the monitoring can be carried out without interference. The lines between the plate elements 20 and 22 refer to the lacquer and a sealing paste. The light conducting fibers are in a position to withstand the pressure resulting from the riveting then and thereafter.

The inventive monitoring can be utilized in several modes of operation. As already mentioned light from a light source can be continuously coupled thereto and the transmission through the light conducting fibers 2 can be monitored by a control person from time to time or continuously by means of light detectors and evaluating electronics. It is however, possible to couple light thereto only when a control person actually carries out the visual inspection or when the inspection is carried out by the evaluating electronics. The inventive measuring device is characterized by a number of advantages over the previous measuring devices. Due to the immediate contact of the light conducting fibers with the upper surface of the construction part the detection sensitivity is considerably increased. Corrosion problems are not to be expected, and in the case of a fracture, the point of light emergence points to the location of the crack. The light conducting fiber is insentitive against electromagnetic stray fields of any kind. A fracture of a fiber once in existence is irreversible so that the crack is indicated even after a load relief on the construction part. Moreover, the cost of these light conducting fibers is very low.

The light conducting fibers 2 can be applied manually or by means of machines under utilizaton of perforated adhesive foils or templates. In the illustration in accordance with FIG. 5, an adhesive foil 10 is seen as a ribbon section which is provided with an areally distributed perforation 11. The example is designed for a diameter of 20 millimeters for the perforation apertures there being correspondingly proportioned spacer pieces. FIG. 6 illustrates a device 12 which permits the installing of light conducting fibers 2 by means of a machine in longitudinal direction on the adhesive side of an adhesive foil ribbon 16. The light conducting fibers are unreeled from a supply spool 25 and at first they are guided through a deflection pulley 27 being disposed in a suction tube 26. The suction tube 26 serves for tensioning the light conducting fibers 2 while the deflection pulley 27 serves also for positioning the fiber advance with the aid of a not illustrated optical positioning measuring device. The light conducting fibers are run via a deflection pulley 28 downstream from the suction tube 26 to pass through a cleaning bath 29 for removing the adhesive paste and a further deflection pulley 30 being disposed above the bath runs the light conducting fibers out of the bath. The cleaned light conducting fibers arrive via a deflection pulley 31 at a deflection pulley 32 towards which is also fed the perforated adhesive foil ribbon 16 from a supply spool 33. The separation paper 34 is first separated from the adhesive foil 16 and is fed via two deflection pulleys 35 and 36 to a deflection pulley 37. The adhesive foil 16 having been provided with the light conducting fibers 2 is now again provided with that separation paper 34 at the deflection pulley 37 and is then fed to a supply spool 36 for storage thereon. Thus the supply spool 38 contains an adhesive foil ribbon 16 which is provided with light conducting fibers 2 and covered by the separation paper 34 so that the ribbon can now be cut to size for purposes of particular measurements. Guide elements such as grooves are provided at one of the deflection pulleys, preferably the deflection pulley 31 which grooves guarantees a definite positioning of the light conductive fibers 2.

In the illustration of FIG. 6a one can see an adhesive foil 16 being provided with light conductive fibers 2 and one can recognize that due to the areal perforation, the light conductive fibers are positioned freely and in uniformly distributed distances from each other. After the pasting upon a test object, the light conductive fibers 2 are free in the range of the perforation apertures and can be fastened to the test object by means of applying (spraying) of a lacquer. After curing of the lacquer layer and removal of the foil, depositing of one and/or several lacquer layers can insure a safe adhesion of the disposed light conductive fibers. One will preferably use zinc chromate lacquer whereby a thinner is used which does not attack the foil, i.e. one will use foil which is resistant against the thinner.

Aside from a positioning of the light conductor fibers in a longitudinal direction of the adhesive foil ribbon 16, it is also possible to provide a meander pattern as for example shown in FIG. 7. Such a positioning requires supplemental equipment such as templates which however is feasible without large expenditure. The adhesive foil ribbon 16 as per FIG. 7 has the light conductive fibers 2 provided with loops which extend beyond the edges. Such a manner of positioning has the advantage that in the case of extendable foil one can compensate for the irregularities that occur in practice with regard to the distance between the rivet holes. This compensation can be provided for upon applying the ribbon to the test object.

For positioning the light conductive fibers 2 in any special pattern one can also use templates. FIGS. 8a and 8b illustrate two templates 39 and 40 which are made of thin, high grade steel sheets and are provided with etched-through tracks 41 and 42 of the light conductive fibers 2. Moreover, these templates 39 and 40 are provided with an anti-adhesion layer which guarantees easy removing after positioning upon an adhesive foil 10. In addition to positioning by means of templates, one can use machines for positioning the light conducting fibers in any configuration. For this one may, for example, use a guide head which deposits the fibers in accordance with an X, Y plotter by means of a microprocessor control in order to obtain any predetermined special pattern. The solution in accordance with the invention permits therefor to dispose light conductive fibers in any configuration on the adhesive side of adhesive foils and to dispose them upon a test object for determining cracks.

The illustration in accordance with FIG. 9a and the corresponding side elevation as per FIG. 9b shows a light conuctive fiber 2 being adheringly disposed upon test object 1. This light conductive fiber 2 is provided with an interruption 50 situated off-center and which is illuminated by a light beam 51 passing light into both portions of the interrupted fiber. The light beam 51 is defocused in the direction of the fiber extension but focused perpendicularly thereto. This insures that upon passing across several closely juxtiposed light conductive fibers just one fiber receives light. A crack 52 has appeared in test object 1 which test object is loaded as illustrated by the arrows. This crack attempts to migrate underneath the light conductive fiber. Additionally one can see from the illustrations of FIGS. 9a and 9b that the interruption 50 as illuminated by the light beam 51 causes light to shine out of the two ends of the light conductive fiber 2. A fracture in the lower fiber portion as a result of the crack 52 is irreversible and leads to a strongly reduced light emission from this end. This change in light can be acquired by means of a photodetector and used for triggering a crack indication or for indicating a crack progression.

In the illustration of FIG. 10 one can also see a test object 1 onto which are pasted ten light conductive fibers $2_1, 2_2, 2_3, \ldots 2_{10}$. These light conductive fibers are respectively provided with interruptions 50 illustrated by a line which interruptions can for example be produced after the fibers have been placed by passing a sharp object such as a needle across them. Respectively elongated photodetectors 53 and 54 are associated with the two ends of the light conductive fibers $2_1, 2_2, \ldots 2_{10}$, and furthermore as explained in FIG. 12, the light conductive fibers are periodically illuminated from a light source by means of a light deflector. Due to the crack 52, the light conductive fibers $2_3, 2_4, 2_5, 2_6, 2_7, 2_8$ are interrupted in their lower parts so that only photodetector 53 will provide one pulse per fiber upon scanning of the interruptions 50. The photodetectors 54 provides pulses only through the fibers $2_1, 2_2,$ and $2_9, 2_{10}$. The pulses as produced herewith are illustrated in the diagram of FIGS. 11a and 11b. Since the pulses in the photodetector 53 are progressively missing as the crack increases, a crack progress indication can be worked out in an evaluating circuit by using the pulses of photodetectors 53 and the pulses of photodetectors 54 as clock pulses.

As already mentioned a light deflector is needed in order to periodically scan the interruptions 50 as provided in the light conductive fibers 2. For this, FIG. 12 illustrates a mirror roll 55 provided with uniform flat surfaces 56. This mirror roll 55 is provided with a not illustrated rotational drive and deflects the light beam 51 which is transmitted by a laser 57 via a deflection mirror 58 and directed towards the mirror roll 55, the deflection as illustrated results in a transverse movement of the light beam across the light conductive fibers 2 which have been pasted on the test object 1. The laser beam 51 is thereby directd towards the interruptions 50 and is focused in the manner described above by means of an astigmatic lens 60 which is provided between the deflection mirror 58 and the mirror roll 55. Upon rotation of the mirror roll 55 by means of a rotational drive, the light beam 51 of the laser 57 passes periodically across the interruptions 50 as provided in the light conductive fibers 2 so that light is coupled briefly into the spots of the fibers.

An evaluating circuit which may, for example, include a computer is therefore in the position to produce a crack progression diagram under utilization of the pulses of the photodetectors 53 and 54 as illustrated in FIGS. 11a and 11b.

FIG. 13 illustrates, for example, such a diagram wherein the crack length is plotted along the ordinate and the number of load cycles is plotted along the abscissa. The FIGS. 1 through 10 on the abscissa are associated with the subscript of the light conductive fibers 2 as per FIG. 10. The crack progression with a number of load cycles or with time can be seen from this diagram because the load cycles are proportional in time.

We claim:

1. Measuring device for determining cracks in test objects by means of a crack detector which includes light conducting fibers comprising, said fibers being pasted to the test object and having interruptions in similar levels;

photo detector means connected to ends of the fibers for producing a signal for indicating a crack in the case of occurrence of cracks;

the light conductive fibers as pasted upon the test object being supplied with light from a light coupler constructed for supplying the several fibers with light through the interruptions and including a deflector that provides for scanning of the interruptions of the fibers; and an evaluating circuit connected to the photo detector means for producing an indication of the crack progression.

2. Measuring device in accordance with claim 1 characterized in that glass fibers are employed as the light conducting fibers (2).

3. Measuring device in accordance with claim 1 characterized in that quartz fibers are used as the light conducting fibers (2).

4. Measuring device in accordance with claim 1 characterized in that fibers of a synthetic material are used as the light conducting fibers (2).

5. Measuring device in accordance with claim 1 characterized in that vapor deposited, light conductive films are used as the light conducting fibers.

6. Measuring device in accordance with claim 1 characterized in that the light conductive fibers (2) are placed in a particular configuration upon the test object, the light conductive fibers being fastened to the test object by means of a thin lacquer coating said light conductive fibers as adhering to the test object being covered with at least one lacquer layer.

7. Measuring device in accordance with claim 6 characterized in that the lacquer layers are comprised of zinc chromate lacquer and are enriched for depositing with a defined thinner.

8. Measuring device in accordance with one of the claims 1 through 7 characterized in that the light conductive fibers are placed upon the test object in a meander pattern.

9. Measuring device in accordance with claim 1 characterized in that numerous light conductive fibers are provided in equidistant spacing parallel upon the test object 1; the interruptions being sufficiently remote from the center of the light conductive fibers.

10. Method of preparing a measuring device for determining cracks in test objects, comprising the steps of;
   placing light conductive fibers in a particular configuration upon an adhesive side of an areally perforated adhesive foil;
   placing the light conductive fibers as adhering to the foils onto the test object and fastening the fibers to the test object through application of lacquer through the perforations of the foil;
   after curing of the lacquer removing the adhesive foil; and
   providing at least one additional lacquer layer on top of said fibers for fastening them additionally to said test object.

11. Method as in claim 10, wherein said adhesive foil is comprised of an extensible material being resistent against a thinner of the lacquer.

12. Method as in claim 10, including the step of placing the light conductive fibers upon the adhesive foil by means of a template, and removing said template from the adhesive foil, there being an anti adhesion layer on the template.

13. Method as in claim 10, including the step of providing the light conductors onto the adhesive foil by means of a guiding head and controlling the guiding head analoguously to an X-Y plotter for depositing the light conductive fibers in a predetermined configuration upon the foil, the configuration being determined by the control of the guiding head.

14. Measuring device for determining cracks in test objects by means of a crack detector which includes light conducting fibers comprising, said fibers being pasted to the test object;
   means connected to the fibers for producing a signal for indicating a crack in the case of occurrence of cracks; light conductive fibers as pasted upon the test object being supplied with light from a laser and a light coupler constructed for supplying the several fibers with light from the laser, and providing an output beam, there being an astigmatic lens for focussing the beam in a direction of beam deflection and for defocussing the beam in a direction of extension of the fibers.

15. Measuring device for determining cracks in test objects by means of a crack detector which includes light conducting fibers comprising, said fibers being pasted to the test object;
   a plurality of photo diodes combined physically in an elongated construction part, the part being connected with one side to ends of the fibers for producing a signal for indicating a crack in the case of occurrence of cracks; and
   the light conductive fibers as pasted upon the test object being supplied with light from a light coupler constructed for supplying the several fibers with light.

* * * * *